US011865242B2

(12) United States Patent
Katz et al.

(10) Patent No.: US 11,865,242 B2
(45) Date of Patent: Jan. 9, 2024

(54) SYSTEM AND METHOD ADDRESSING PREMATURE PROCEDURE TERMINATION (71) Applicant: Fenwal, Inc., Lake Zurich, IL (US)

(72) Inventors: Steven R. Katz, Deerfield, IL (US); Dale H. Meixelsperger, Gurnee, IL (US); Roberto Vilardi, Antioch, IL (US)

(73) Assignee: Fenwal, Inc., Lake Zurich, IL (US)

( * ) Notice: Subject to any disclaimer, the term of this patent is extended or adjusted under 35 U.S.C. 154(b) by 724 days.

(21) Appl. No.: 16/893,115

(22) Filed: Jun. 4, 2020

(65) Prior Publication Data

US 2020/0384182 A1    Dec. 10, 2020

Related U.S. Application Data (60) Provisional application No. 62/858,770, filed on Jun. 7, 2019.

(51) Int. Cl.
*A61M 1/36* (2006.01)
*G16H 40/67* (2018.01)
(Continued)

(52) U.S. Cl.
CPC ........ *A61M 1/3621* (2013.01); *A61M 1/3622* (2022.05); *A61M 60/113* (2021.01); *A61M 60/279* (2021.01); *A61M 60/36* (2021.01); *A61M 60/508* (2021.01); *A61M 60/849* (2021.01); *G16H 10/20* (2018.01); *G16H 40/67* (2018.01); *A61M 2202/0413* (2013.01); *A61M 2205/18* (2013.01)

(58) Field of Classification Search
CPC .......... A61M 1/3621; A61M 60/113; A61M 60/279; A61M 60/36; A61M 60/508; A61M 2205/52; A61M 60/849; A61M 2202/0413; A61M 2205/18; A61M 1/02; A61M 1/3693; G16H 10/20; G16H 40/67; G16H 20/40; G16H 40/06
USPC .......................................................... 604/48
See application file for complete search history.

(56) References Cited

U.S. PATENT DOCUMENTS 5,360,542 A   11/1994 Williamson, IV et al.
5,868,696 A   2/1999 Giesler et al.
(Continued)

OTHER PUBLICATIONS

European Patent Office, Extended European Search Report, counterpart EP Appl. No. 20178649 (dated Oct. 9, 2020) (8 pages).

*Primary Examiner* — Joy Chng
(74) *Attorney, Agent, or Firm* — Cook Alex Ltd.

(57) ABSTRACT

A medical system includes a reusable apparatus and a disposable fluid circuit, the disposable fluid circuit being coupled to the reusable apparatus and the reusable apparatus being configured to move a fluid through the disposable fluid circuit to perform a procedure. The medical system also includes a controller coupled to the reusable apparatus and configured to control the reusable apparatus to move the fluid through the disposable circuit according to the procedure, to store a procedure record in a memory, to await a procedure termination input, and if the procedure termination input is received, to request at least one input corresponding to a procedure termination reason and to add the procedure termination reason corresponding to the input to the procedure record if received.

20 Claims, 8 Drawing Sheets

(51) Int. Cl.
*G16H 10/20* (2018.01)
*A61M 60/849* (2021.01)
*A61M 60/508* (2021.01)
*A61M 60/113* (2021.01)
*A61M 60/279* (2021.01)
*A61M 60/36* (2021.01)

(56) References Cited

U.S. PATENT DOCUMENTS

| | | |
|---|---|---|
| 6,565,802 B1 | 5/2003 | Hanley et al. |
| 7,025,877 B1 * | 4/2006 | de Gheldere ......... A61L 2/0082 422/561 |
| 2003/0220598 A1 | 11/2003 | Busby et al. |
| 2004/0088189 A1 * | 5/2004 | Veome ................ A61M 1/3681 530/382 |
| 2016/0175510 A1 * | 6/2016 | Patel .................. G05D 16/2066 137/12 |
| 2018/0361054 A1 * | 12/2018 | Roxas ................ A61M 1/1601 |

* cited by examiner

SYSTEM AND METHOD ADDRESSING PREMATURE PROCEDURE TERMINATION

CROSS-REFERENCE TO RELATED APPLICATIONS

This application claims the benefit of U.S. Provisional Patent App. No. 62/858,770, filed Jun. 7, 2019, which is expressly incorporated herein by reference in its entirety.

TECHNICAL FIELD

The present disclosure is generally directed to a system and method for processing a biological fluid, and in particular a biological fluid processing system or method where the processing may be terminated prematurely.

BACKGROUND

Blood processing systems may be configured to process blood drawn from a patient and to return the processed fluid to the patient, according to a procedure. These blood processing systems may include a reusable processor or separator, as well as a disposable fluid circuit or set that is connected to the patient. The set may also be connected to various containers that include other fluids, such as blood products, solutions and the like.

During a typical instance of such a procedure, the blood processing system processes the blood drawn from a beginning of the procedure to an end of the procedure. Not all instances of the procedure run from the beginning to the end, however. Sometimes, an issue will arise that will require the blood processing system to prematurely terminate an instance of the procedure. Other times, an issue will arise that will cause an operator of the blood processing system to prematurely terminate an instance of the procedure.

During the procedure, the system may generate a considerable amount of data relating to the procedure. For instance, the system may include sensors that provide information about events that occur during the procedure. The system may analyze this data to provide alerts to the operator regarding the operation of the system. The system may also analyze this data to determine if a condition has occurred that requires the system to prematurely terminate the procedure. The system may further analyze this data to determine if a condition has occurred that requires the system to determine if the operator wishes to terminate the procedure prematurely.

Despite, or perhaps as a consequence of, the volume of data generated, it may be difficult to determine the reason or reasons why a procedure terminated prematurely. The advantages are immediately apparent of a system configured to reduce the data clutter, or conversely to bring greater clarity to the data generated. At the same time, adoption of a system that is configured to reduce the data clutter or bring greater clarity will be hampered if the changes to the system require the system to change the manner in which the procedure is performed, or that require substantial changes to the manner in which the operator interacts with the system.

SUMMARY

In an aspect of the disclosure, a medical system includes a reusable apparatus and a disposable fluid circuit, the disposable fluid circuit being coupled to the reusable apparatus and the reusable apparatus being configured to move a fluid through the disposable fluid circuit to perform a procedure. The medical system also includes a controller coupled to the reusable apparatus and configured to control the reusable apparatus to move the fluid through the disposable circuit according to the procedure, to store a procedure record in a memory, to await a procedure termination input, and if the procedure termination input is received, to request at least one input corresponding to a procedure termination reason and to add the procedure termination reason corresponding to the input to the procedure record if received.

DETAILED DESCRIPTION

A detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
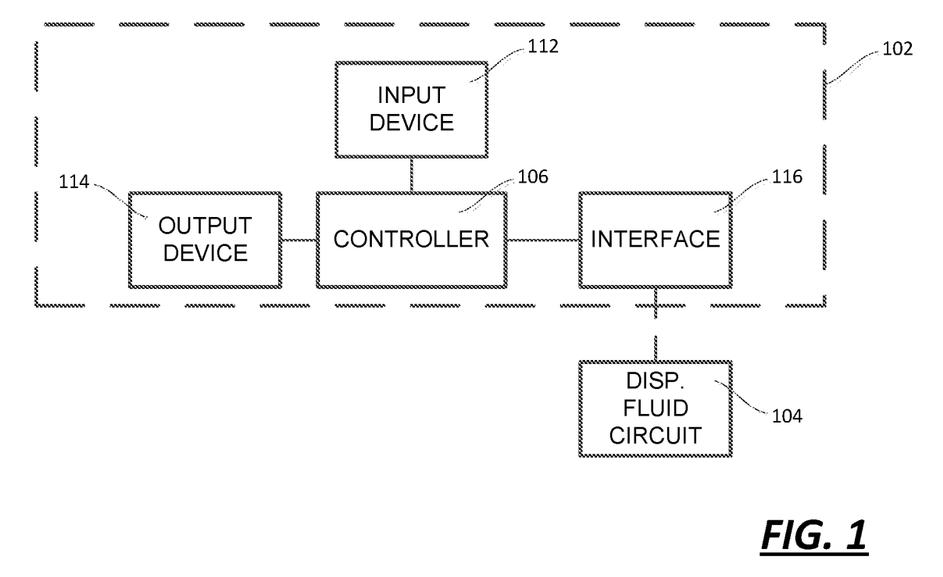
FIG. 1 is a block diagram of an embodiment of a medical system including a reusable apparatus and a disposable processing set or fluid circuit.

In general terms, and as illustrated in FIG. 1, a medical system 100 includes a reusable apparatus 102 and a disposable fluid circuit 104, the disposable fluid circuit 104 coupled to the reusable apparatus 102 and the reusable apparatus 102 configured to move a fluid through the disposable fluid circuit 104 to perform a procedure.

According to certain embodiments, as will be explained in detail and illustrated in FIGS. 7-10, the reusable apparatus 102 is an apheresis device and the disposable fluid circuit 104 is an apheresis set. In such an embodiment, the apheresis device 102 may include at least one pump and the disposable fluid circuit 104 is mounted on the pump, the pump being configured to move the fluid through at least a section of the disposable fluid circuit 104.

Figure 2:
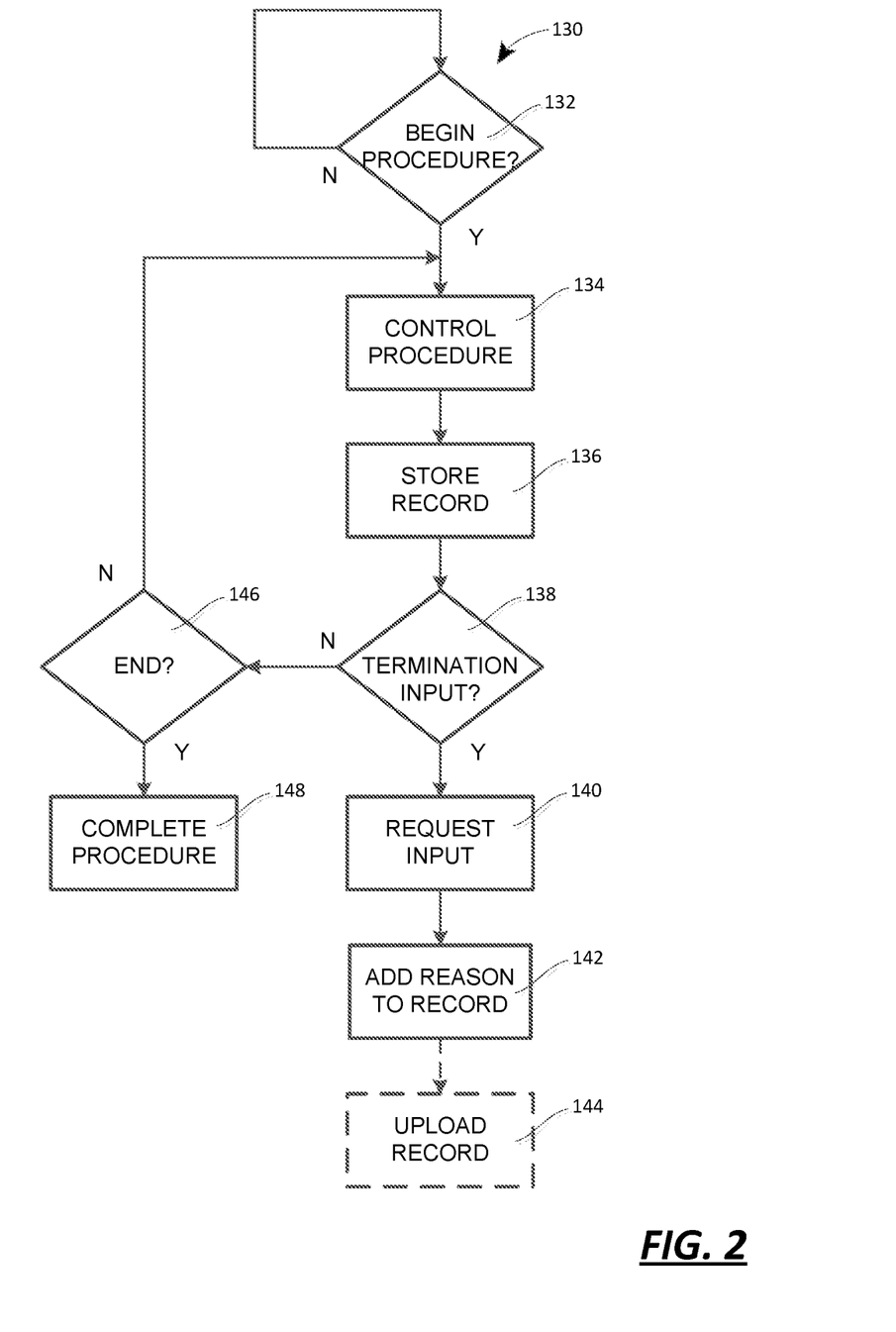
FIG. 2 is a flowchart of a method of operating a medical system, such as the medical system according to FIG. 1 or FIG. 3.

The medical system 100 also includes a controller 106, the controller 106 being coupled to the reusable apparatus 102, which may include being part of the reusable apparatus 102 as illustrated. According to embodiments, as illustrated in FIG. 2, the controller 106 may be configured to control the reusable apparatus 102 to move the fluid through the disposable circuit 104 according to the procedure, to store a procedure record in a memory, to await a procedure termination input, and, if the procedure termination input is received, to request at least one input corresponding to a procedure termination reason and to add the procedure termination reason corresponding to the input to the procedure record if received.

Figure 3:
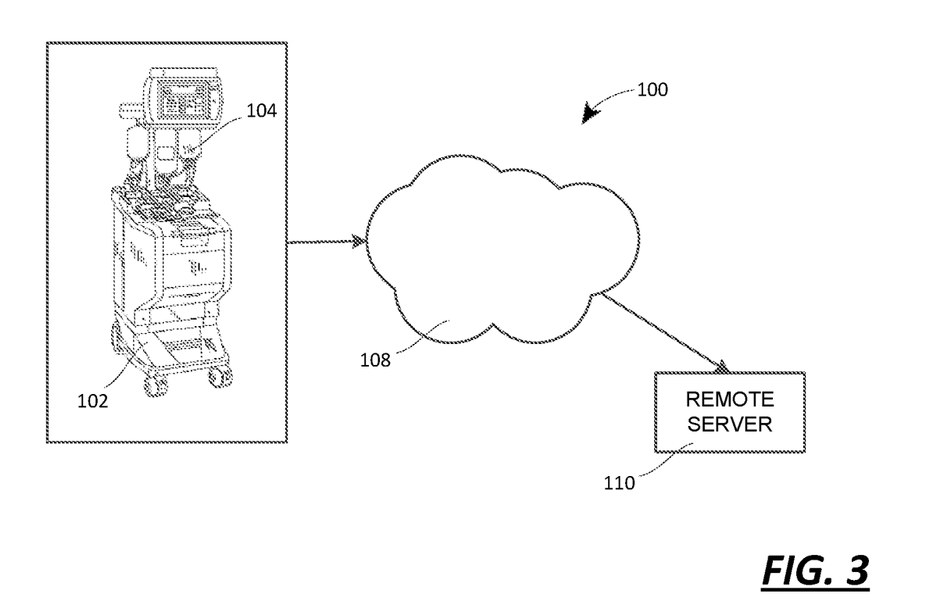
FIG. 3 is a schematic diagram of the medical system of FIG. 1, including additional features of a network and a server on which is maintained a database.

According to a further embodiment of the medical system 100, the medical system 100 may include a network 108 and a remote database 110, as illustrated in FIG. 3. The controller 106 may be coupled to the remote database 110 via the network 108. According to this embodiment, the controller 106 may be configured to transmit the procedure record to the remote database 110 after the one of the plurality of procedure termination reasons is added to the procedure record.

Having discussed the structure and operation of the medical system 100 in general terms, the details are now discussed starting with FIG. 1.

As noted above, the reusable apparatus 102 includes the controller 106, which may include one or more programmable microprocessors (which, in turn, may include multiple physical and/or virtual processors). Alternatively, the controller 106 may include one or more electrical circuits designed to carry out the actions described herein. In fact, the controller 106 may include one or more microprocessors as well as other circuits or circuitry. The controller 106 may also include and one or more memories coupled to the one or more programmable microprocessors, which memories may be referred to as coupled to the controller 106 even though they, in fact, are part of the controller 106. The instructions by which the microprocessor is programmed may be stored on the memory/memories associated with the microprocessor, which memory/memories may include one or more tangible non-transitory computer readable memories, having computer executable instructions stored thereon, which when executed by the microprocessor, may cause the microprocessors to carry out one or more actions as described below. The memory/memories may also be used to store data, such as is described below.

The reusable apparatus 102 may include, in addition to the controller 106, an input device 112 and an output device 114. The input device 112 and the output device 114 may be integrated into a single structure, such as where the input device 112 is a touchscreen and the output device 114 is an electronic display. The input device 112 may also include pointing devices (e.g., a stylus, a mouse, or a touchpad), keypads, keyboards, and scanners (e.g., a barcode scanner or an RFID scanner), by way of illustration and not by way of limitation. Further, the output device 114 may be an electronic display separate and apart from the input put device 112. The input device 112 and the output device 114 may be coupled to the controller 106 to permit the controller 106 to receive one or more inputs, as explained below, and to display information regarding the operation of the reusable apparatus 102, as is also explained below.

The reusable apparatus 102 may also include an interface 116 that engages the disposable fluid circuit 104 or that is engaged by the disposable fluid circuit 104. For example, the interface 116 may include a pump (such as a peristaltic pump) which receives a length of a line of the disposable fluid circuit 104. The interface 116 may include valves, such as pinch valves, that engage one or more lines of the fluid circuit 104 to control the flow and direction of flow of fluid in the lines of the fluid circuit 104. According to some embodiments, the fluid circuit 104 may include a cassette that has flow paths with selectable junctions defined therein, which flow paths cooperate with the interface 116 at the selectable junctions to permit the interface 116 to control the flow and direction of flow of fluid in the fluid circuit 104. The interface 116 may also include, for example, a spool element that engages with a processing container of the fluid circuit 104 to apply centrifugal force to the contents of the processing container and to separate the contents into components thereby. The interface 116 may include all of the aforementioned structures, or only certain combinations thereof.

As noted above, the medical system 100 may include not only the reusable apparatus 102 but a network 108 and a remote database 110 as well, as illustrated in FIG. 3. In particular, the controller 106 may be coupled to the network 108, which may be a hard-wired network, a wireless network, or a combination thereof, and via the network 108 to a server 110 on which the database is maintained. The server 110, like the controller 106, may include one or more programmable microprocessors (which, in fact may include multiple physical and/or virtual processors), one or more electrical circuits, and one or more memories coupled to the one or more programmable microprocessors. The instructions by which the microprocessor is programmed may be stored on the memory/memories associated with the microprocessor, which memory/memories may include one or more tangible non-transitory computer readable memories, having computer executable instructions stored thereon, which when executed by the microprocessor, may cause the microprocessors to carry out one or more actions. The memory/memories may also be used to store the data that is included in the database 110. The controller 106 and the server 110 each may be coupled to a networking device (e.g., a networking card, a transceiver, or the like). that cooperates with the network 108 to permit communication (which may be either one-way or two-way communication) between the devices 102 and 110. According to some embodiments, it may be possible for the apparatus 102 to communicate directly with the server 110 without the necessity of an intermediate network 108, depending on the equipment installed in the apparatus 102 and the server 110.

According to certain embodiments, the server 110 may be disposed in a different part of a room from the reusable device 102. Alternatively, the server 110 may be disposed in a different part of the same building as the reusable device 102, or in a different city, state or country from the reusable device 102. According to all of these embodiments, the server 110 may be referred to as a remote server.

While a single reusable device 102 is illustrated in FIG. 3 as connected by the network 108 to the server 110, this arrangement should not be taken as limiting. A plurality of reusable devices 102 may be connected to the server 110 by the network 108. Further, the network 108 may itself represent a combination of both local networks and wider-area networks, such as the Internet. In addition, while the database and the server have been referred to interchangeably relative to the embodiment illustrated in FIG. 3, the database may be maintained on more than a single server. In fact, the database or copies of the database may be maintained on a plurality of servers.

Further, input and output devices may be coupled to the server 110 to permit the database to be accessed and edited.

According to certain embodiments, the server 110 may be accessed by computing devices over the network 108, permitting persons to operate those computing devices (which devices may each include processors and memories, and have input and output devices coupled thereto) to access, analyze and edit the database located at the server (or servers) 110. For example, a user located at such a computing device may analyze the data maintained in the database 110 relative to the reusable device(s) 102 to draw conclusions regarding the operation of the reusable device(s) 102 or the operators using those reusable device(s) 102.

As next regards the operation of the medical system 100, a first embodiment of a method 130 is illustrated in FIG. 2. As noted above, the controller 106 may be configured to carry out this embodiment of the method 130, as well as any of the other embodiments of the method 130 illustrated in FIGS. 4-6. According to some embodiments, the controller 106 may comprise a microprocessor and one or more memories, and the processor may be programmed to carry out the illustrated embodiments of the method according to instructions stored in the one or more memories.

The method 130 starts a block 132, where the controller 106 determines if it is time to begin the procedure. According to certain embodiments, the controller 106 may determine that it is time to begin the procedure when a "start" key is depressed. According to other embodiments, the controller 106 may determine that it is time to begin the procedure once certain preliminary steps have been performed, for example once a check has been performed to determine that the disposable circuit 104 has been mounted correctly on the reusable apparatus 102 (e.g., on the interface 116) and the disposable circuit 104 has been primed with fluid.

The method continues to block 134, where the controller 106 controls the reusable apparatus 102 (e.g., the pumps, the valves, and the rotating separator element) to control the reusable apparatus 102 to move the fluid through the disposable circuit 104 according to the procedure. The controller 106 may also be configured to cause the display 114, if one is provided, to display information to the operator. This information may involve events, such as machine states occurring during the procedure, or alerts, such as may cause the reusable apparatus 102 to be stopped, temporarily or permanently, relative to the instance of the procedure being performed and, according to certain events, the operator to be prompted to take action.

The method 130 further includes a block 136, where the controller 106 stores data (or information) in a record for the procedure (i.e., a procedure record). While the block 136 follows block 134 in FIG. 2, the controller 106 may store data in a record for the procedure at the same time or even before the control of the procedure at block 134 begins, with the procedure record being constantly modified and updated as part of the method 130. The procedure record may include data on the events and alerts that occur during the procedure. The procedure record may also include data regarding the apparatus 102, the set 104, the patient (if present) and the operator(s) attending the apparatus 102 during the instance of the procedure being performed. The data that is stored in the procedure record may be received from one or more sensors (which sensors may be included in the input devices 112) or from a touchscreen, keypad, barcode scanner or the like (also included in the input devices 112). This data may be stored in a memory coupled to (or part of) the controller 106 as part of a data file or other storage structure, for example. According to other embodiments, the data may be stored in a memory that is connected to the apparatus 102 via a network as well as stored in a memory coupled to (or part of) the controller 106, or even instead of being stored in a memory coupled to (or part of) the controller 106.

The controller 106 then checks for a termination input at block 138. If controller 106 determines that the procedure termination input has been generated or received, then the controller 106 requests at least one input corresponding to a procedure termination reason at block 140 and adds the procedure termination reason corresponding to the input (if received) to the procedure record at block 142. According to certain embodiments, the controller 106 may be configured or programmed to delay or stop operation until the input is received in response to the request, as explained in detail below. According to other embodiments, the method 130 may simply terminate if no input is received.

The input may be a selection input of a procedure termination reason from a plurality of procedure termination reasons. The plurality of procedure termination reasons may be displayed in a list, such as on the display 114 or in a written form. Where the list is displayed on a display 114, the selection input may be received via a touch screen, for example. Where the list is displayed in written form, each reason in the list may have a machine-readable code (e.g., a barcode) attached thereto (e.g., printed on the list at a location proximate to a location where the reason is printed), and the input may be received through the use of an input device 112 in the form of a reader (e.g., a barcode reader) that can read the machine-readable code and can send a signal to the controller 106 corresponding to the machine-readable code that was read and thus the reason selected. As a further alternative, the controller 106 may be configured to prompt the operator for a reason, whereupon the operator uses the input device 112 (e.g., in the form of a touchscreen or keyboard) to enter the reason freestyle (i.e., without a predetermined plurality of procedure termination reasons being provided).

As a still further alternative, the controller 106 may be configured to present the operator with (e.g., display) one or more questions, to receive one or more answers from the operator to the one or more questions, for example via the input device 112, and to use the answers either as a selection input or to select a selection input based on the one or more answers. According to such an embodiment, the questions may be in the form of a fixed set that is presented (e.g., displayed) to the operator, or the answers may cause the questions presented to the operator to vary (i.e., a dynamic set), in that different questions may be presented based on an answer received to a prior question, for example. The controller 106 may also be configured to vary the questions based on a current state of the medical system (e.g., a state that caused a recoverable or non-recoverable alert to be generated). Further, it will be recognized that the one or more questions according to such an embodiment may be editable, for example being edited by an party using the input device 112 or by a party accessing the questions via the network 108, which questions may be stored in the memory coupled to the controller 106 when edited or downloaded to the memory from a remote location where the party accesses and edits the questions.

According to certain embodiments, the controller 106 may be configured to receive a single input corresponding to a single procedure termination reason; other embodiments may differ. That is, the controller 106 may be configured to receive a single input corresponding to multiple procedure termination reasons, or to receive multiple inputs each input corresponding to a single or multiple procedure termination reasons. Consequently, the references previously to an input are intended to include all such options unless a specific option is particularly identified. It will be recognized that while a single input and a single reason may provide the most compact (and perhaps most efficient) interaction with the system 100, it may be desirable to provide greater flexibility in the input choices to permit a more detailed identification of the basis or bases for terminating the instance of the procedure prematurely.

As noted above, the method 130 optionally may include transmitting the record (with the procedure termination reason (or reasons) added thereto) to a database 110. Accordingly, the method 130 of FIG. 2 includes a block 144 where the controller 106 may upload the record to the database 110. It will be recognized that the upload that may occur at block 144 may or may not utilize the network 108. For example, it may be possible to transfer the procedure record to a portable memory storage device (e.g., a memory disk or stick) which is then transported to the server 110 for upload to the database.

As is also illustrated in FIG. 2, the method 130 may continue if the controller 106 determines at block 138 that a termination input has not been received. In particular, the controller 106 may determine if the instance of the procedure has reached its end at block 146. For example, the procedure may have predefined or preprogrammed end conditions, such as when a certain amount of fluid has been processed, stored or consumed. According to such an embodiment, when the end condition is achieved, the method 130 continues to block 148 with the controller 106 causing the apparatus 102 to end the procedure. While the end of the procedure may involve ceasing the operation of the apparatus 102, the end of the procedure at block 148 may also include activities such as the sealing and removal of one or more product containers and the uploading of the procedure record to the database 110. If the controller 106 determines the end of the procedure has not occurred at block 146, the method 130 returns to block 134.

It will be recognized that the order of the actions illustrated in FIG. 2 has been selected mainly for ease of explanation, and not to limit the embodiment of the method 130 to only the order illustrated in FIG. 2. For example, the actions at blocks 134 and 136 may occur simultaneously or in parallel, rather than sequentially or serially. It may even be possible for the determinations at blocks 138 and 146 to come before the actions at blocks 134 and 136, and for the determinations at blocks 138 and 146 to be reversed. It will be recognized that those actions that follow from block 138 or 146 would still follow as illustrated even if the determinations at blocks 138 and 146 come before the actions at blocks 134 and 136, for example. It will also be recognized that if the condition recited at blocks 138 and 146 is phrased opposite that illustrated (e.g., whether a termination input is absent, or whether the procedure is to continue), the actions that follow blocks 138 and 146 would follow a negative determination instead of a positive determination as illustrated.

Figure 4:
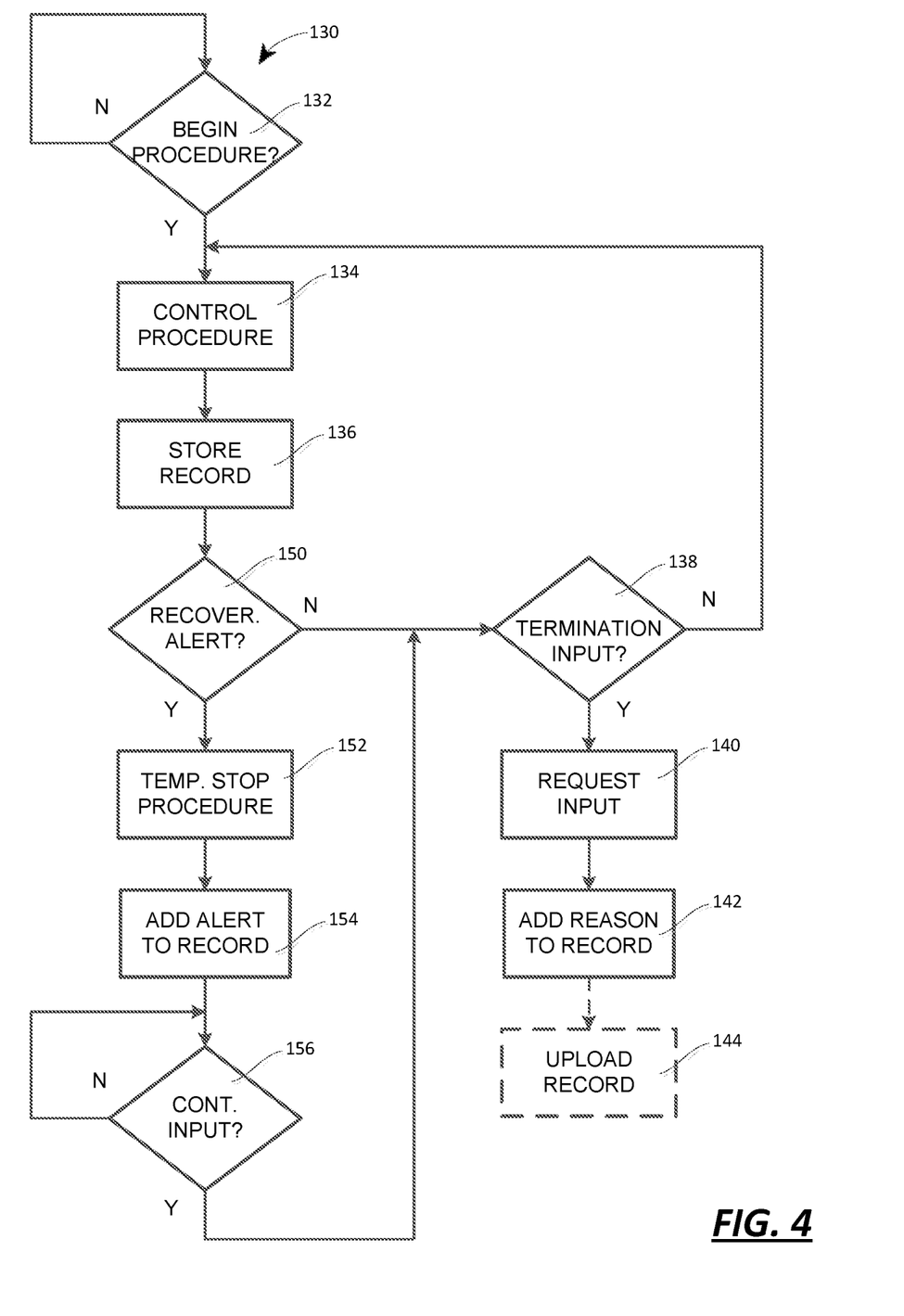
FIG. 4 is a flowchart of a method of operating a medical system, such as the medical system according to FIG. 1 or FIG. 3, addressing (at least) recoverable alerts.
Figure 5:
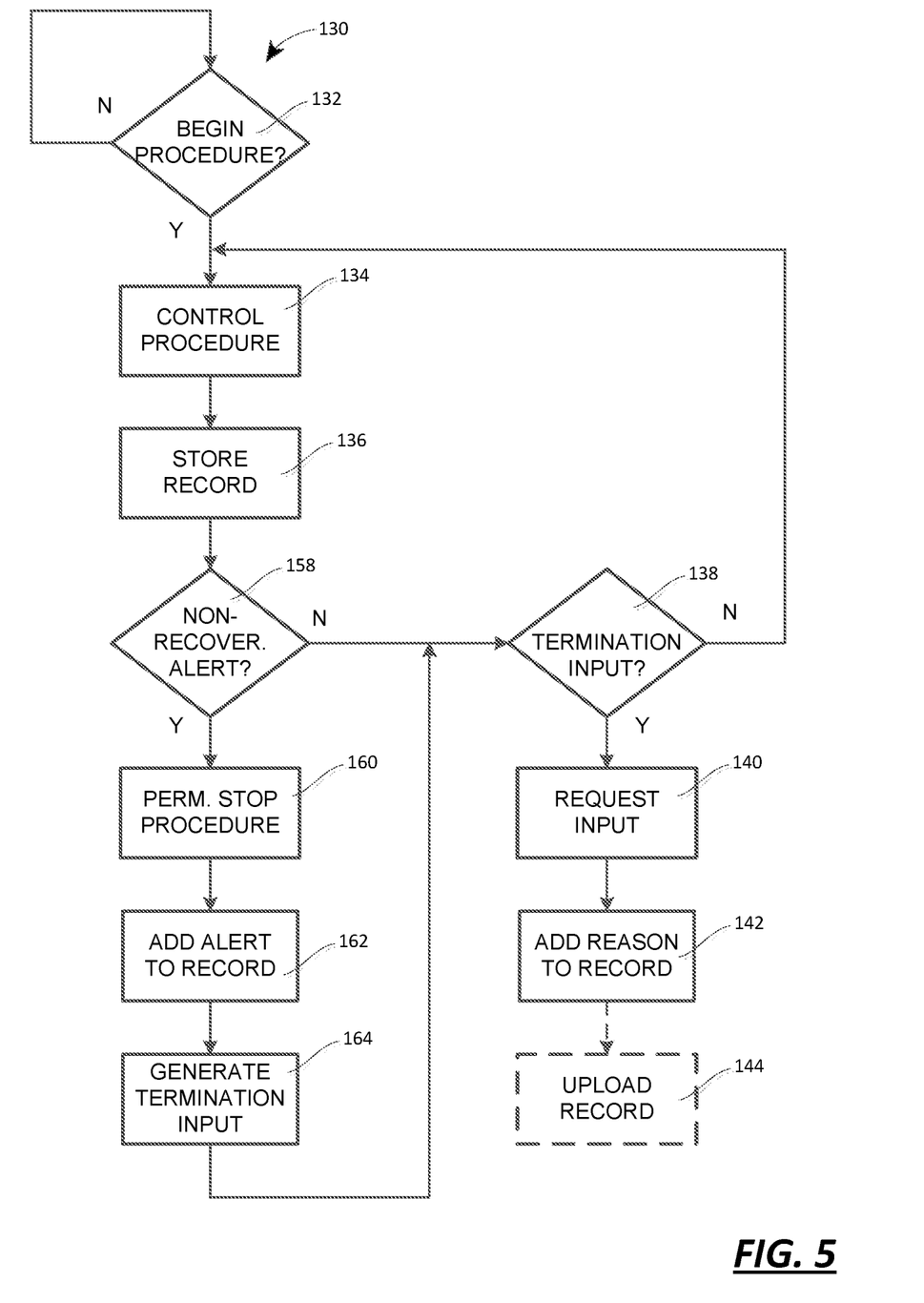
FIG. 5 is a flowchart of a method of operating a medical system, such as the medical system according to FIG. 1 or FIG. 3, addressing (at least) non-recoverable alerts.
Figure 6:
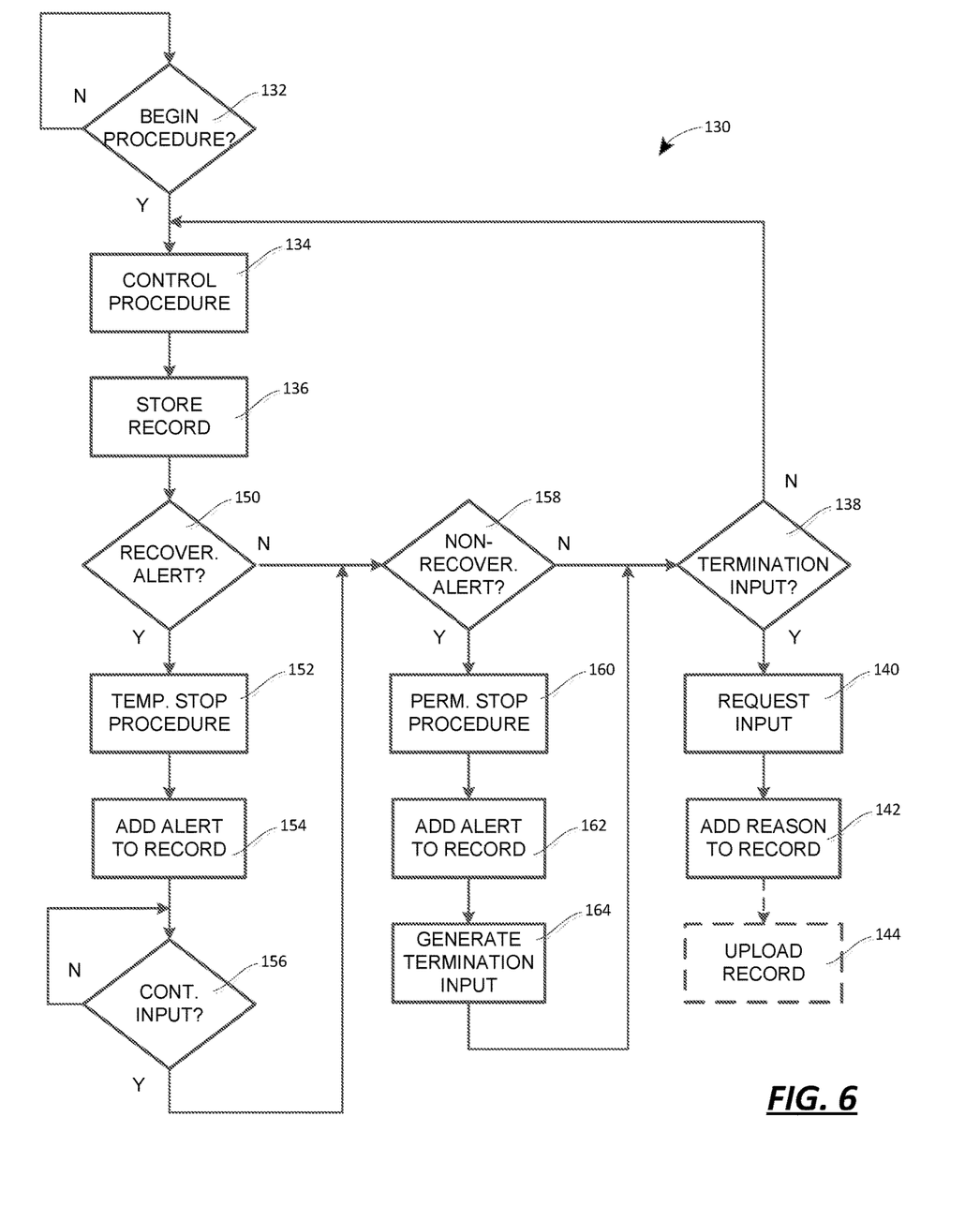
FIG. 6 is a flowchart of a method of operating a medical system, such as the medical system according to FIG. 1 or FIG. 3, addressing (at least) both recoverable and non-recoverable alerts.

The method 130 may include additional steps, as reflected in the embodiments of FIGS. 4-6. The same reference numerals are used in FIGS. 4-6 as in FIG. 2 for actions that are common to the various embodiments of method 130. Because the actions shared in common have been discussed in detail above, the discussion is not repeated herein. Furthermore, to simplify the flowcharts of FIGS. 4-6, the actions of blocks 146, 148 are not included in the embodiments of the method 130 illustrated in FIGS. 4-6, although it will be recognized that these embodiments of the method 130 would still make the determination whether the end of the procedure has been reached and take actions based on this determination.

The embodiment of the method illustrated in FIG. 4 begins in a similar fashion as the embodiment of the method 130 illustrated in FIG. 2: the controller 106 determines if the procedure is to begin (block 132), and then controls the reusable apparatus to carry out the procedure (block 134) and stores a procedure record for the procedure in a memory coupled to the controller 106 (block 136). The embodiment of the method 130 in FIG. 4 differs in that the controller 106 determines if a recoverable alert has been generated by the reusable apparatus 102 at block 150.

A recoverable alert is an alert that does not require that the instance of the procedure be terminated. Because a recoverable alert does not require that the instance of the procedure be terminated, the apparatus 102 may not generate a procedure termination input automatically. On the other hand, the operator may manually input a procedure termination input, through the manipulation of an input device (e.g., input device 112). For example, the operator may actuate a virtual stop button and a virtual end button on a touchscreen/display to manually input a procedure termination input.

The recoverable alert may be connected to an issue that can be resolved by the operator. For example, a recoverable alert may be connected to an occluded line in the disposable fluid circuit 104, which occluded line may be the result of a bend in one or more of the lines of the circuit 104. The operator may resolve such an issue by ensuring that the lines are straight.

The status of an issue as a recoverable alert may be assigned by the manufacturer of the reusable apparatus 102. Alternatively, a hierarchy of operators may exist relative to a reusable apparatus 102, with certain operators (which may be referred to as administrators) having the authority to assign an issue as a recoverable alert, while other operators do not have this authority. It may also be the case that certain recoverable alerts assigned by the manufacturer may be reassignable by administrators, while other recoverable alerts cannot be reassigned by administrators.

If the controller 106 determines that at least one recoverable alert has occurred at block 150, the method 130 of FIG. 4 passes to block 152, where the controller 106 temporarily stops (or pauses) operation of the reusable apparatus 102 so as to temporarily stop (or pause) the procedure. The stop is temporary in that the intent is for the operator to be able to continue the procedure once the alert has been addressed. The controller 106 then adds add the at least one recoverable alert to the procedure record in the memory at block 154.

At block 156, the controller 106 awaits receipt of a continuation input. The continuation input may be received via the same input device used elsewhere in the method 130, for example to signal the beginning of the procedure. If the input is not received, the controller 106 continues to wait at block 156. If the controller 106 determines that the continuation input has been received, then the method 130 resumes the procedure upon receipt of the continuation input and passes to block 138.

According to certain alternative embodiments, the controller 106 may not await the receipt of a continuation input, and thus the method 130 would not include the action of block 156. The method 130 would instead include only the actions of blocks 152, 154, after which point the method would pass to block 138. As a further alternative, the controller 106 may proceed to block 138 after waiting for an amount of time to pass after the alert has been added to the record at block 154. In either case, the controller 106 would automatically recover from the alert, and would not wait for an input from the operator.

As explained above, the controller 106 determines at block 138 if a termination input has been generated or received. If it has not, the method 130 returns to block 134 (after checking to determine if the end of the procedure has occurred). If it has, then the method 130 continues to blocks 140 and 142, optionally followed by block 144.

The embodiment of the method 130 illustrated in FIG. 5 begins in a similar fashion as the embodiments illustrated in FIGS. 2 and 4: the controller 106 determines if the procedure is to begin (block 132), and then controls the reusable apparatus to carry out the procedure (block 134) and stores a procedure record for the procedure in a memory coupled to the controller 106 (block 136). The method 130 of FIG. 5 differs in that the controller 106 operating according to the embodiment of the method 130 illustrated in FIG. 5 determines if a non-recoverable alert has been generated by the reusable apparatus at block 158.

A non-recoverable alert is an alert that requires that the instance of the procedure be terminated. Because a non-recoverable alert requires that the instance of the procedure be terminated, the apparatus 102 may generate a procedure termination input automatically. Alternatively, the controller 106 may prompt the operator to manually input a procedure termination input, through the manipulation of an input device (e.g., input device 112).

The non-recoverable alert may be connected to an issue that cannot be resolved by the operator. For example, a failure in the mechanical or electrical components of the reusable apparatus 102 may represent a non-recoverable alert.

The status of an issue as a non-recoverable alert may be assigned by the manufacturer of the reusable apparatus 102. Alternatively, an administrator may assign an issue as a non-recoverable alert. It may also be the case that certain non-recoverable alerts assigned by the manufacturer may be reassigned by administrators, while other non-recoverable alerts cannot be reassigned by administrators.

If the controller 106 determines that at least one non-recoverable alert has occurred at block 158, the method 130 of FIG. 5 passes to block 160, where the controller 106 permanently stops operation of the reusable apparatus 102 so as to permanently stop the instance of the procedure. The stop is permanent in that the intent that the instance of the procedure cannot be resumed. The controller 106 then adds the at least one non-recoverable alert to the procedure record in the memory at block 162. At block 164, the controller 106 generates a termination input. As discussed above, alternatively, the controller 106 may prompt the operator to manually input a termination input.

As explained above, the controller 106 determines at block 138 if a termination input has been generated or received. If it has not, the method 130 returns to block 134. If it has, then the method 130 continues to blocks 140 and 142, optionally followed by block 144.

A still further embodiment of the method is illustrated in FIG. 6, and begins in a similar fashion as the method illustrated in FIGS. 2, 4, and 5: the controller 106 determines if the procedure is to begin (block 132), and then controls the reusable apparatus to carry out the procedure (block 134) and stores a procedure record for the procedure in a memory coupled to the controller 106 (block 136). The method 130 of FIG. 6 differs in that the controller 106 operating according to the embodiment of the method 130 illustrated in FIG. 6 determines if a recoverable alert has been generated by the reusable apparatus (block 150) or if a non-recoverable alert has been generated by the reusable apparatus (block 158) as well as determining if a termination input has been received (block 138).

As is illustrated in FIG. 6, if the controller 106 determines that a recoverable alert has been received at block 150, then the method 130 continues with blocks 152-156 (or, optionally, blocks 152, 154). Similarly, if the controller 106 determines that a non-recoverable alert has been received at block 158, then the method 130 continues with blocks 160-164. The controller 106 then determines at block 138 if a termination input has been generated or received. If it has not, the method returns to block 134; if it has, then the method continues to blocks 140 and 142, optionally followed by block 144.

In addition to the actions described relative to the blocks of the embodiments of method 130 illustrated in FIGS. 2 and 4-6, the methods 130 may include additional optional actions as well.

For example, according to certain embodiments, the controller 106 may permit operation of the reusable apparatus 102 even if the input of the termination procedure reason is not received. That is, the input of the termination procedure reason may be optional. According to other embodiments, however, the controller 106 is configured to prevent operation of the reusable apparatus 102 until the at least one input corresponding to the procedure termination reason is received. That is, the reusable apparatus 102 may not be used to perform another instance of the procedure (or of any procedure) until the input corresponding to the procedure termination reason(s) is/are received relative to the instance of the procedure that was terminated prematurely.

As mentioned above, the at least one input corresponding to the procedure termination reason may be a selection input corresponding to one of a plurality of procedure termination reasons. Further, the controller 106 may be coupled to a display (e.g., display 114), and the controller 106 may be configured to display the plurality of procedure termination reasons on the display. Consequently, the methods 130 may include a block disposed between the block 138 and the block 140 or immediately after block 140, wherein the controller 106 controls the display to display the plurality of procedure termination reasons.

As a part of any of the embodiments of the method 130, the plurality of procedure termination reasons may be editable. This editing action may be taken at the controller 106, may be taken remotely via at a computing device, or may be distributed over a network to a plurality of reusable apparatuses 102 (and in particular the controllers 106 coupled thereto). The plurality of procedure termination reasons also may be editable in the sense that, where the plurality of procedure termination reasons are in printed form and associated with machine-readable codes (e.g., barcodes), the operator may write a new reason to be added to the plurality and may associate that written reason with a specific machine-readable code.

In fact, according to certain embodiments, the controller 106 is configured to edit the plurality of procedure termination reasons according to at least one of a recoverable alert, a non-recoverable alert, and an event. For example, one or more blocks may be disposed between the block 138 and the block 140, wherein the controller 106 determines the nature of any events or alerts contained in the procedure record, and then edits the plurality of procedure termination events to exclude certain reasons and/or include certain reasons based on the events and alerts. As a result, the plurality of procedure termination events depends, at least in part, on the nature of the event(s) or alert(s) occurring during the instance of the procedure leading to the premature termination.

As a further part of any of the embodiments of the method 130, the controller 106 may transmit the termination reason or reasons to a complaint system. The complaint system may include one or more servers, and may even include or incorporate the server with database 110. The server or servers of the complaint system may include one or more programmable microprocessors (which, in fact may include multiple physical and/or virtual processors), one or more electrical circuits, and one or more memories coupled to the one or more programmable microprocessors. The instructions by which the microprocessor is programmed may be stored on the memory/memories associated with the microprocessor, which memory/memories may include one or more tangible non-transitory computer readable memories, having computer executable instructions stored thereon, which when executed by the microprocessor, may cause the microprocessors to carry out one or more actions. The servers may be coupled to a networking device (e.g., a networking card, a transceiver, or the like). that cooperates with the network 108 to permit communication (which may be either one-way or two-way communication) between the devices 102 and 110 and the server or servers of the complaint system. According to certain embodiments, the server or servers of the complaint system may be accessed by computing devices over the network 108, permitting persons to operate those computing devices (which devices may each include processors and memories, and have input and output devices coupled thereto) to access, analyze and edit the complaints transmitted to the server or servers of the complaint system and stored in a complaint database.

The transmission of the termination reason or reasons to the complaint system may provide a more direct and active route for the termination reason or reasons to become or be made available to stakeholders (e.g., the manufacturer) that have a role in modification of the structure and/or operation of the device(s) 102. That is, while appending the termination reason or reason(s) to the record may improve the nature of the record for future use, the transmission of the termination reason or reasons to the complaint system does not require for the user to wait for an interested party, such as a stakeholder, to analyze the record. Instead, the user can make their desire to see the device 102 or its method of operation modified by forwarding their termination reason or reasons to the complaint system, which may be actively monitored by the stakeholders, such as the manufacturer, or may provide active prompts to the stakeholders.

The transmission of the termination reason or reasons to the complaint system may occur at the same time as the transmission of the record to the database 110. In fact, where the database 110 is part of the complaint system, the transmission of the record to the database 110 may automatically trigger the complaint system to register the transmission of the record as a complaint. Alternatively, the termination reason or reasons, with or without the remainder of the record, may be transmitted to the complaint system, either automatically or at the request of the user.

The automated transmission of the termination reason or reasons (with or without the remainder of the record) may occur in all instances where a termination reason is provided, or the controller 106 may be programmed to transmit only certain termination reasons to the complaint system. For example, the automated transmission of the reason may occur for all non-recoverable alerts, or only certain classes of non-recoverable alerts, such as non-recoverable alerts that relate to a particular component of the device 102. According to other embodiments, the nature of the termination reason or reasons may cause the termination reason or reasons to be transmitted to the complaint system and registered by the complaint system as a complaint. The automated transmission may even occur in a semi-manual fashion, where the controller 106 is programmed or controller to provide a prompt to the user, recommending that the user transmit the termination reason or reasons to the complaint system and requesting their confirmation. The prompt may be provided for a static list of termination reasons, or the prompt may be dynamic, in that the prompt is provided based on the responses from the user to a list of questions. This prompt-based embodiment may provide an added advantage of causing the user to recognize that their input has been forwarded to the stakeholders for action in a way that a fully automated transmission of the termination reason or reasons might not.

In response to the transmission of the termination reason or reasons, with or without the remainder of the record, to the complaint system, the complaint system may register the complaint in the system. As alluded to above, the registration of the complaint in, for example, a complaint database may encourage the parties (e.g., stakeholders) who monitor the complaint database to take action relative to the termination reason or reasons, such as a modification to the hardware, software or disposable associated with the device 102, and may even prompt the parties to review the termination reason or reasons by sending an electronic communication (e.g., an email or text) to the stakeholders to make them aware of the need for review. Alternatively, the complaint system may not actively prompt the parties, but the complaint database may simply provide another source of data that may be accessed and analyzed. The complaint system may also be coupled to other systems that use the data to schedule updates to the devices 102.

As another part of any of the embodiments of the method 130, the controller 106 may be configured to receive an input via an input device (e.g., the input device 112) corresponding to an operator identifier (such as an identification code or number) and to store the operator identifier in the procedure record. According to certain embodiments, where the operator identifier is in the form of a machine-readable code (e.g., a barcode) printed on an operator badge, a code scanner (e.g., a barcode scanner) may be used to receive the identifier; alternatively, a touchscreen or keypad may be used to enter the identifier. Such action may be taken prior to block 132 (wherein it is determined that the procedure is beginning) or after block 138 (wherein it is determined that a termination input has been generated or received), for example. In fact, such action may occur both when the procedure is initiated (block 132) and when the termination input is entered (e.g., prior to block 138) or it is determined that a termination input has been entered (after block 138). In this fashion, the identity of the operator who set up the procedure and the identity of the operator who terminated the procedure may be preserved for later analysis, as well as whether the operators are the same person.

Figure 7:
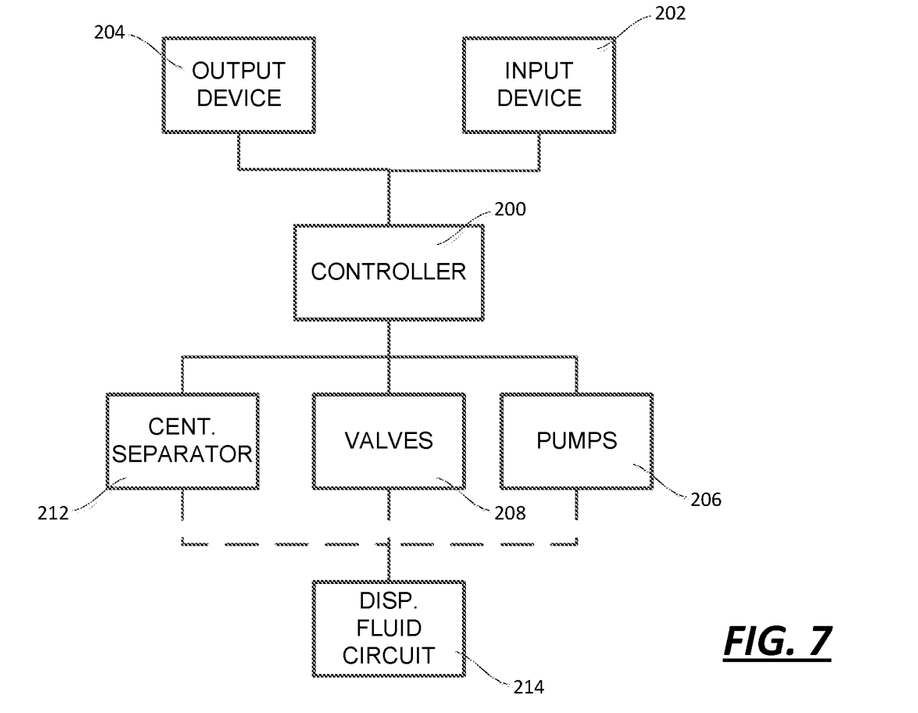
FIG. 7 is a block diagram of another embodiment of a medical system including a reusable apparatus and a disposable processing set or fluid circuit.
Figure 8:
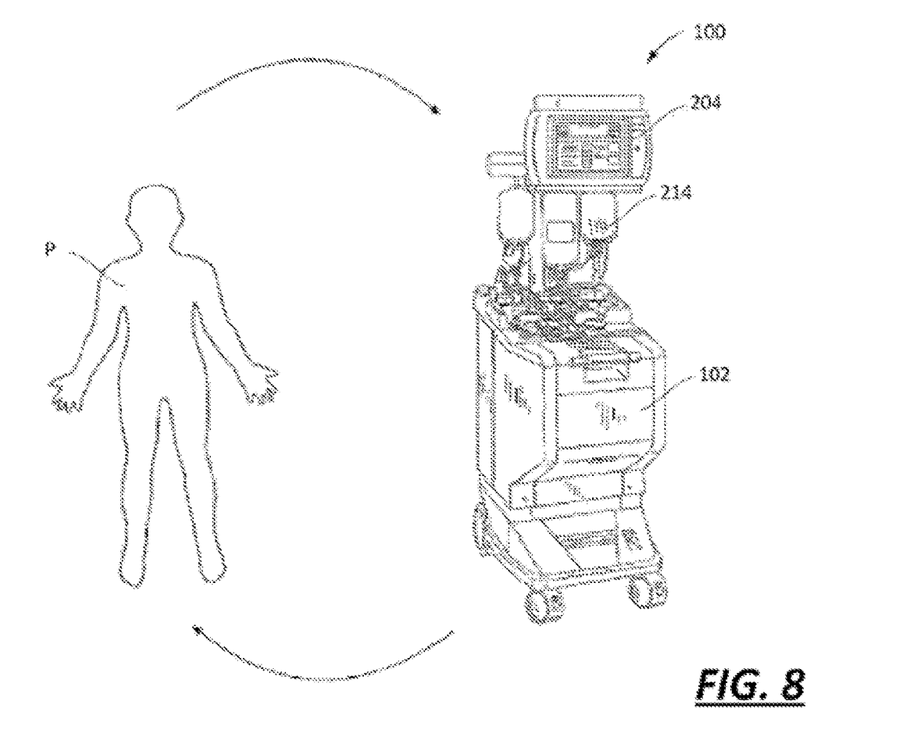
FIG. 8 is a schematic diagram of the medical system of FIG. 7.
Figure 9:
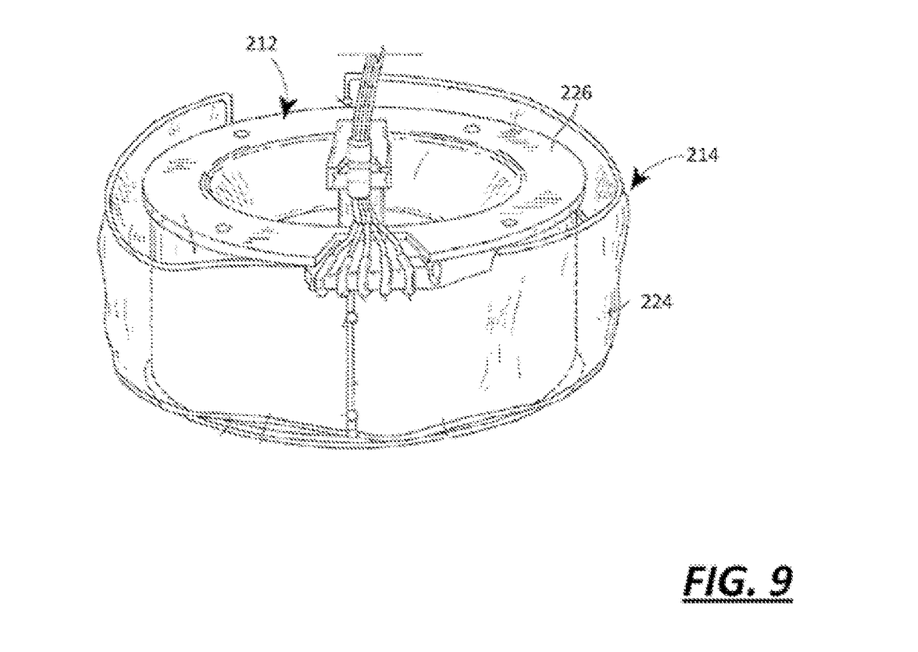
FIG. 9 is a schematic diagram of a sub-system of the medical system of FIG. 7.
Figure 10:
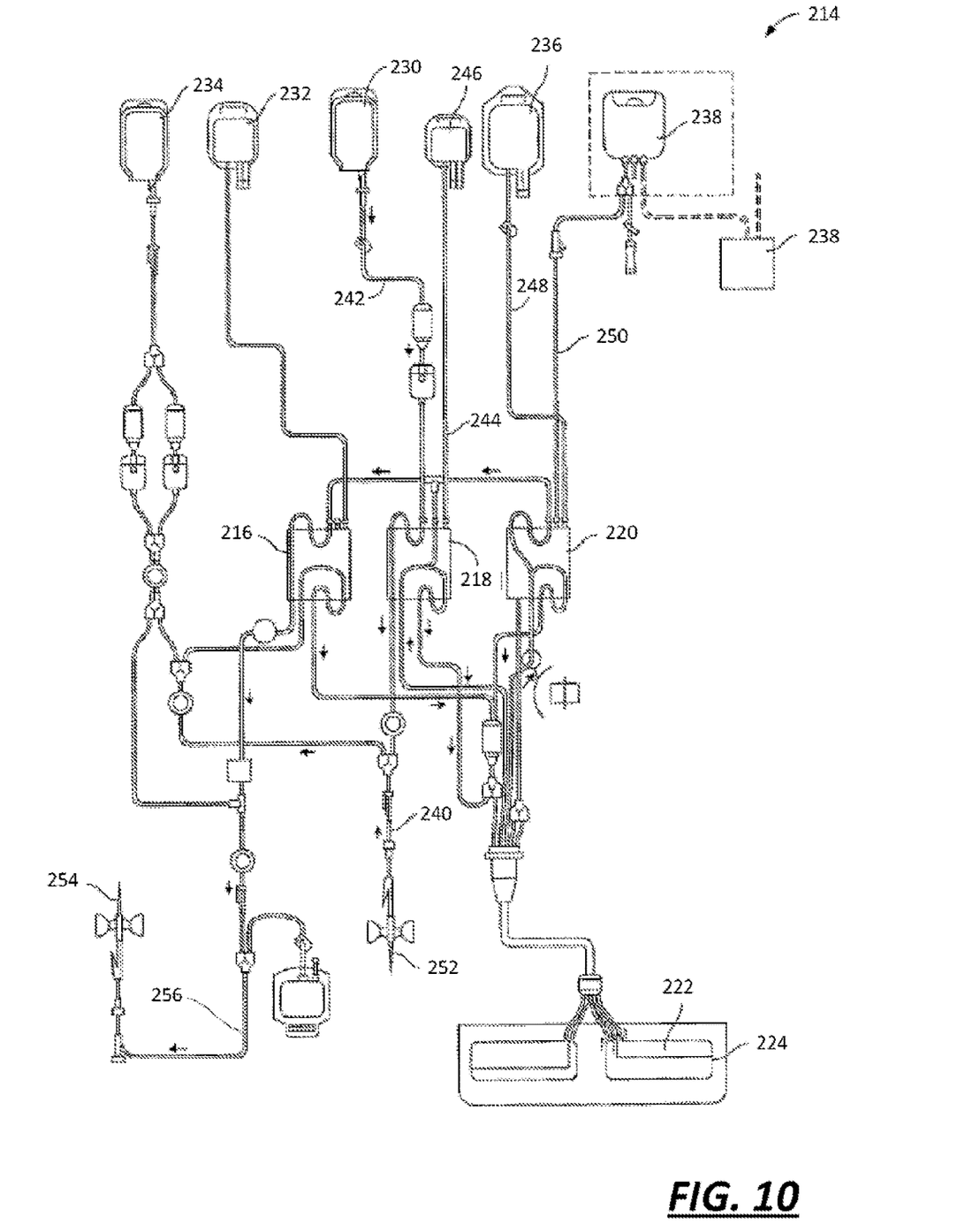
FIG. 10 is a schematic diagram of a fluid circuit used in the medical system of FIGS. 7-9.

As mentioned above, according to certain embodiments of the medical system 100, the reusable device 102 may be an AMICUS® Separator, available from Fresenius Kabi USA, Lake Zurich, Illinois, configured to carry out apheresis. Briefly, FIGS. 7-10 show such an embodiment of an apparatus 102, with FIG. 7 illustrating the structures of the apparatus 102 schematically, FIG. 8 illustrating the structures of the apparatus 102 in greater detail in association with a patient P, FIG. 9 illustrating a representative blood centrifuge (defining part of the apparatus 102) with a portion of a fluid circuit mounted thereon (which fluid circuit may be an embodiment of the fluid circuit 104), and FIG. 10 illustrating the entire fluid circuit. Additional details of the interaction of such an apparatus and a set are discussed in U.S. Pat. No. 5,868,696, which is incorporated by reference herein in its entirety.

With reference first to FIG. 7, the illustrated embodiment of the apparatus 102 thus may include a controller 200, which may be configured as the controller 106 discussed above, and in particular may be configured to carry out one (or more) of the embodiments of the method 130 illustrated in FIGS. 2 and 4-6. The apparatus also includes an input device 202 in the form of a touch screen and an output device 204 in the form of an electronic display, such as the embodiments of the input device 112 and output device 114 discussed above. The input devices 202 according to this embodiment may further include sensors (or sensor stations), such as weight scales, pressure sensors and air detectors. The controller 200 is coupled to the input devices 202 and the output device 204, as well as to a plurality of pumps 206 (e.g. peristaltic pumps), a plurality of valves (or valve stations) 208, and a centrifugal separator 212. Mounted on the pumps 206, the valves 208, and the separator 212 (which along with the sensors 202 may together define an embodiment of the interface 116) is a fluid circuit 214, which may be an embodiment of the fluid circuit 104. The controller 200 is configured (e.g., programmed) to control each of the pumps 206, valves 208, and the separator 212 to carry out an instance of a procedure in combination with the fluid circuit 214.

Processing set (also referred to as a fluid circuit) 214 includes a plurality of processing fluid flow cassettes 216, 218, 220 (see FIG. 10) with tubing loops for association with peristaltic pumps 206. Set 214 also includes a network of tubing and connected (or pre-connected) containers for establishing flow communication with the patient and for processing and collecting fluids and blood and blood components, as discussed in detail below. The set 214 also includes a separation chamber 222.

As illustrated in FIGS. 9 and 10, the separation chamber 222 is defined by the walls of a flexible processing container 224 carried within an annular gap defined by a rotating spool element 226 (see FIG. 9) and an outer bowl element of the device. The processing container 224 takes the form of an elongated tube that is wrapped about the spool element 226 before use. The bowl and spool element 226 are pivoted on a yoke between an upright position and a suspended position. In operation, the centrifuge 212 rotates the suspended bowl and spool element 226 about an axis, creating a centrifugal field within the processing chamber 222 of container 224. Details of the mechanism for causing relative movement of the spool 226 and bowl elements as just described are disclosed in U.S. Pat. No. 5,360,542, the contents of which is also incorporated by reference herein in its entirety.

As seen in FIG. 10, the disposable processing set 214 may include the flexible processing container 224, as well as additional containers, such as a container 230 for supplying anticoagulant, a waste container 232 for collecting waste from one or more steps in a process, a container 234 for holding saline or other wash or resuspension medium, a container 236 for collecting plasma, as well as other containers 238. The set 214 also may include inlet line 240, an anticoagulant (AC) line 242 for delivering AC from container 230, an RBC line 244 for conveying red blood cells from chamber 222 of container 224 to a container 246, a platelet-poor plasma (PPP) line 248 for conveying PPP to container 236 and line 250 for conveying other fluids to and from separation chamber 222 and the containers 238. In addition, the blood processing set 214 includes one or more venipuncture needle(s) for accessing the circulatory system of the patient. As shown in FIG. 10, set 214 includes an inlet needle 252 attached to the inlet line 240 and a return needle 254 attached to a return line 256; in an alternative embodiment, a single needle can serve as both the inlet and outlet needle.

Fluid flow through set 214 is preferably driven, controlled and adjusted by the controller 200 in cooperation with the pumps 206, valves 208, and sensors 202, the details of which are described in the previously mentioned U.S. Pat. No. 5,868,696. In a general sense, blood is drawn from the patient via the inlet needle 252 into the inlet line 240, where it passes through one or more of the cassettes 216, 218, 220 and may be processed in the processing chamber 222. The containers 230, 232, 234, 236, 238, 246 are also connected via the cassettes 216, 218, 220 to the processing chamber 222, and fluids may be drawn from or passed to the containers 230, 232, 234, 236, 238, 246 as a consequence of the operation of the cassettes 216, 218, 220 and the chamber 222 (and associated pumps and spool/bowl element). Fluid is returned to the patient along return line 122 via return needle 254.

OTHER ASPECTS

Aspect 1. A medical system comprising:
a reusable apparatus and a disposable fluid circuit, the disposable fluid circuit coupled to the reusable apparatus and the reusable apparatus configured to move a fluid through the disposable fluid circuit to perform a procedure;
a controller coupled to the reusable apparatus and configured:
to control the reusable apparatus to move the fluid through the disposable circuit according to the procedure;
to store a procedure record in a memory;
to await a procedure termination input;
if the procedure termination input is received, to request at least one input corresponding to a procedure termination reason and to add the procedure termination reason corresponding to the input to the procedure record if received.
Aspect 2. The medical system according to aspect 1, wherein the controller is configured:
to receive at least one recoverable alert from the reusable apparatus during the procedure;
to temporarily stop the procedure upon receipt of the at least one recoverable alert from the reusable apparatus;
to add the at least one recoverable alert to the procedure record in the memory; and
to await receipt of a continuation input and to resume the procedure upon receipt of the continuation input.
Aspect 3. The medical system according to aspect 2, wherein the at least one recoverable alert comprises an occlusion alert.
Aspect 4. The medical system according to any one of the preceding aspects, further comprising an input device, wherein the controller is configured to receive the procedure termination input from the input device.
Aspect 5. The medical system according to aspect 1, wherein the controller is configured:

to receive at least one non-recoverable alert from the reusable apparatus during the procedure;
to permanently stop the procedure upon receipt of the at least one non-recoverable alert from the reusable apparatus;
to add the at least one non-recoverable alert to the procedure record in the memory; and
to generate the procedure termination input.

Aspect 6. The medical system according to any one of the preceding aspects, wherein the controller is configured to prevent operation of the reusable apparatus until the at least one input corresponding to the procedure termination reason is received.

Aspect 7. The medical system according to any one of the preceding aspects, wherein the at least one input corresponding to the procedure termination reason is a selection input corresponding to one of a plurality of procedure termination reasons.

Aspect 8. The medical system according to aspect 7, wherein the controller is coupled to a display device, and the controller is configured to display the plurality of procedure termination reasons on the display device.

Aspect 9. The medical system according to aspect 8, wherein the plurality of procedure termination reasons is editable.

Aspect 10. The medical system according to aspect 9, wherein the controller is configured to edit the plurality of procedure termination reasons according to at least one of a recoverable alert, a non-recoverable alert, and an event.

Aspect 11. The medical system according to aspect 7, wherein the controller is configured to present one or more questions, to receive one or more answers to the one or more questions, and to use the one or more answers as one or more selection inputs or to select one or more selection inputs based on the one or more answers.

Aspect 12. The medical system according to aspect 11, wherein the controllers is configured to vary the one or more questions presented based on the one or more answers received.

Aspect 13. The medical system according to aspect 11 or 12, wherein the controller is configured to vary the one or more questions presented based on a current state of the medical system.

Aspect 14. The medical system according to any one of aspects 11 to 13, wherein the one or more questions is editable.

Aspect 15. The medical system according to any one of the preceding aspects, wherein the controller is configured to add at least one event occurring during the procedure to the procedure record.

Aspect 16. The medical system according to any one of the preceding aspects, further comprising an input device coupled to the controller, the controller configured to receive an input via the input device corresponding to an operator ID and to store the operator ID in the procedure record.

Aspect 17. The medical system according to any one of the preceding aspects, further comprising a network and a remote database, the controller coupled to the remote database via the network, wherein the controller is configured to transmit the procedure record to the remote database after the one of the plurality of procedure termination reasons is added to the procedure record.

Aspect 18. The medical system according to any one of the preceding aspects, wherein the reusable apparatus is an apheresis device and the disposable fluid circuit is an apheresis set.

Aspect 19. The medical system according to aspect 18, wherein the apheresis device includes at least one pump and the disposable fluid circuit is mounted on the pump, the pump being configured to move the fluid through at least a section of the disposable fluid circuit.

Aspect 20. The medical system according to any one of the preceding aspects, wherein the controller is configured to transmit the procedure termination reason corresponding to the input, if received, to a complaint system

The invention claimed is:

1. A medical system comprising:
a reusable apparatus and a disposable fluid circuit, the disposable fluid circuit coupled to the reusable apparatus and the reusable apparatus configured to move a fluid through the disposable fluid circuit to perform a procedure;
a controller coupled to the reusable apparatus and configured:
to control the reusable apparatus to move the fluid through the disposable fluid circuit according to the procedure;
to store a procedure record for the procedure in a memory;
to determine whether an alert has been generated by the reusable apparatus, and if the alert has been generated, to stop the reusable apparatus depending on the alert, and to add the alert to the procedure record;
to await a procedure termination input; and
if the procedure termination input is received, to request at least one input corresponding to a procedure termination reason and to add the procedure termination reason corresponding to the input to the procedure record if received.

2. The medical system according to claim 1, wherein the alert is at least one recoverable alert and the controller is configured:
to receive the at least one recoverable alert from the reusable apparatus during the procedure;
to temporarily stop the procedure upon receipt of the at least one recoverable alert from the reusable apparatus;
to add the at least one recoverable alert to the procedure record in the memory; and
to await receipt of a continuation input and to resume the procedure upon receipt of the continuation input.

3. The medical system according to claim 2, wherein the at least one recoverable alert comprises an occlusion alert.

4. The medical system according to claim 1, further comprising an input device, wherein the controller is configured to receive the procedure termination input from the input device.

5. The medical system according to claim 1, wherein the alert is at least one non-recoverable alert and the controller is configured:
to receive the at least one non-recoverable alert from the reusable apparatus during the procedure;
to permanently stop the procedure upon receipt of the at least one non-recoverable alert from the reusable apparatus;
to add the at least one non-recoverable alert to the procedure record in the memory; and
to generate the procedure termination input.

6. The medical system according to claim 1, wherein the controller is configured to prevent operation of the reusable apparatus until the at least one input corresponding to the procedure termination reason is received.

7. The medical system according to claim 1, wherein the at least one input corresponding to the procedure termination reason is a selection input corresponding to one of a plurality of procedure termination reasons.

8. The medical system according to claim 7, wherein the controller is coupled to a display device, and the controller is configured to display the plurality of procedure termination reasons on the display device.

9. The medical system according to claim 8, wherein the plurality of procedure termination reasons is editable.

10. The medical system according to claim 9, wherein the controller is configured to edit the plurality of procedure termination reasons according to at least one of a recoverable alert, a non-recoverable alert, and an event.

11. The medical system according to claim 7, wherein the controller is configured to present one or more questions, to receive one or more answers to the one or more questions, and to use the one or more answers as one or more selection inputs or to select one or more selection inputs based on the one or more answers.

12. The medical system according to claim 11, wherein the controller is configured to vary the one or more questions presented based on the one or more answers received.

13. The medical system according to claim 11, wherein the controller is configured to vary the one or more questions presented based on a current state of the medical system.

14. The medical system according to claim 11, wherein the one or more questions is editable.

15. The medical system according to claim 1, wherein the controller is configured to add at least one event occurring during the procedure to the procedure record.

16. The medical system according to claim 1, further comprising an input device coupled to the controller, the controller configured to receive an input via the input device corresponding to an operator ID and to store the operator ID in the procedure record.

17. The medical system according to claim 1, further comprising a network and a remote database, the controller coupled to the remote database via the network, wherein the controller is configured to transmit the procedure record to the remote database after the one of the plurality of procedure termination reasons is added to the procedure record.

18. The medical system according to claim 1, wherein the reusable apparatus is an apheresis device and the disposable fluid circuit is an apheresis set.

19. The medical system according to claim 18, wherein the apheresis device includes at least one pump and the disposable fluid circuit is mounted on the pump, the pump being configured to move the fluid through at least a section of the disposable fluid circuit.

20. The medical system according to claim 1, wherein the controller is configured to transmit the procedure termination reason corresponding to the input, if received, to a complaint system.

* * * * *